(12) United States Patent
Vallittu et al.

(10) Patent No.: US 7,235,290 B2
(45) Date of Patent: Jun. 26, 2007

(54) PREPREG, A COMPOSITE AND THEIR USES

(75) Inventors: Pekka Vallittu, Kuusisto (FI); Lippo Lassila, Turku (FI); Antti Yli-Urpo, Littoinen (FI)

(73) Assignee: Stick Tech Oy, Turku (FI)

( * ) Notice: Subject to any disclaimer, the term of this patent is extended or adjusted under 35 U.S.C. 154(b) by 418 days.

(21) Appl. No.: 10/479,809

(22) PCT Filed: Jun. 12, 2002

(86) PCT No.: PCT/FI02/00508

§ 371 (c)(1),
(2), (4) Date: Dec. 5, 2003

(87) PCT Pub. No.: WO02/100355

PCT Pub. Date: Dec. 19, 2002

(65) Prior Publication Data

US 2004/0166304 A1    Aug. 26, 2004

Related U.S. Application Data

(60) Provisional application No. 60/297,268, filed on Jun. 12, 2002.

(30) Foreign Application Priority Data

Jun. 12, 2001    (FI) .................................. 20011233

(51) Int. Cl.
*B32B 25/02*    (2006.01)
*B32B 5/26*    (2006.01)
*A61C 13/12*    (2006.01)

(52) U.S. Cl. ................ 428/296.7; 433/220; 433/221.1; 433/180; 442/269; 442/204

(58) Field of Classification Search ............. 428/296.7, 428/292.1, 370; 433/220, 221.1, 180; 442/269, 442/204
See application file for complete search history.

(56) References Cited

U.S. PATENT DOCUMENTS

| | | | | |
|---|---|---|---|---|
| 3,906,550 | A | | 9/1975 | Rostocker et al. ............ 3/1.912 |
| 4,132,215 | A | * | 1/1979 | Burton ....................... 124/35.2 |
| 4,894,012 | A | | 1/1990 | Goldberg et al. ........... 433/215 |
| 5,127,783 | A | * | 7/1992 | Moghe et al. ............... 411/411 |
| 5,580,626 | A | * | 12/1996 | Quigley et al. ............. 428/36.2 |
| 5,676,546 | A | | 10/1997 | Heitmann et al. ........ 433/199.1 |
| 5,723,007 | A | | 3/1998 | Engel et al. .................. 623/11 |
| 5,816,816 | A | | 10/1998 | Scharf ......................... 433/220 |
| 5,839,900 | A | | 11/1998 | Billet et al. ................. 433/218 |

(Continued)

FOREIGN PATENT DOCUMENTS

| | | |
|---|---|---|
| FI | 102946 B | 3/1999 |
| GB | 2 214 087 A | 8/1989 |

*Primary Examiner*—N Edwards
(74) *Attorney, Agent, or Firm*—James C. Lydon (57) ABSTRACT

A prepreg containing fibers and a curable matrix, the prepreg having a core and a surface part encasing the core, where the matrix of the core and of the surface part are made of the same material and where the proportion of the matrix to the fibers is higher in the core than in the surface part. A composite obtainable from the prepreg as well as the use of the composite or prepreg are also disclosed.

22 Claims, 10 Drawing Sheets

U.S. PATENT DOCUMENTS

| | | | |
|---|---|---|---|
| 5,846,640 A | 12/1998 | Vallittu | 428/306.6 |
| 5,919,044 A | 7/1999 | Sicurelli, Jr. et al. | 433/220 |
| 5,921,778 A | 7/1999 | Karmaker et al. | 433/215 |
| 6,045,571 A * | 4/2000 | Hill et al. | 606/228 |
| 6,197,410 B1 | 3/2001 | Vallittu et al. | 428/292.1 |
| 6,334,775 B2 * | 1/2002 | Xu et al. | 433/228.1 |
| 6,827,576 B2 * | 12/2004 | Karmaker et al. | 433/220 |

* cited by examiner

PREPREG, A COMPOSITE AND THEIR USES

This application is a U.S. National Stage of International application PCT/FI02/00508, filed Jun. 12, 2002, and which claims priority of U.S. provisional application No. 60/297,268, filed Jun. 12, 2001 and Finnish patent application 20011233, filed Jun. 12, 2001.

FIELD OF INVENTION

The present invention relates to a prepreg comprising fibers and a curable matrix. The invention further relates to a composite obtainable from such a prepreg as well as to the use of said prepreg or composite.

BACKGROUND OF THE INVENTION

Many dental and medical devices made from polymers or composites need to bond or adhere to other materials, such as other resins or composites, or to living tissue, such as bone. In dentistry, it has been found that the adhesion of polymerised fiber reinforced composite having a thermosetting polymer matrix made for example of a copolymer of 2,2-bis(4-(2-hydroxy-3-methacryloxy)phenyl)propane (Bis-GMA) and triethyleneglycoldimethacrylate (TEGDMA) to a new polymeric material is difficult to obtain. Poor adhesion can result in e.g. debonding of parts of the composite, loosening or delamination of a root canal post made from said composite.

The problem has partly been resolved by the invention described in patent application WO 99/45890 (Vallittu et al.) where a thermoplastic membrane was used to cover the thermosetting polymer matrix of the prepreg. The thermoplastic membrane allowed adhesion of the new polymeric material by means of interdiffusion (interpenetrating polymer network).

In other medical applications of fiber-reinforced composites, like in orthopaedic implants (e.g. hip prostheses), there is a need to achieve bonding of bone to the implant. The technique of roughening the surface of the implant has most widely been used to increase the bonding of the metal surface of the implant to the bone, together with the help of acrylic bone cements. Clinical experience has shown that a relatively great number of detachments of endosseus implant prostheses occur after five to ten years use of the prosthesis.

Numerous publications disclose the use of prepregs and composites in medicine. U.S. Pat. No. 4,894,012 discloses passive dental appliances of fiber-reinforced composites being fully impregnated with composite. U.S. Pat. No. 5,921,778 discloses a hybrid woven material formed of glass yarns and synthetic yarns to prevent fray upon cutting. U.S. Pat. No. 5,919,044 discloses a flexible post in a dental post and core system. U.S. Pat. No. 5,816,816 discloses a method of producing a dental post for use in restoring or stabilizing one or more teeth. The method includes the steps of creating a hole in a tooth and obtaining a woven hollow rope, which is mounted over a mandrel and inserted into the hole. Patent application DE 29 32 435 discloses a hip joint and a dental implant having fiber structure on a metal core.

U.S. Pat. No. 5,723,007 discloses a biocompatible composite material with a plastic matrix having a felt of collagen fibers contained therein, wherein the collagen fibers project out from the surface of the material so that it can be colonized with human cells prior to implantation. The material is manufactured by impregnating collagen fibers with a matrix, partially curing said matrix and removing the unpolymerized matrix. The fibers that project out from the surface of the material are thus partially covered by said matrix.

GB 2 214 087 discloses a composite canal post wherein the surface is mechanically roughened in order to increase the bonding strength of the surface. In U.S. Pat. No. 5,839,900 a dental prosthesis is proposed in which the surface is treated by abrasion or erosion to expose the fibers.

U.S. Pat. No. 5,676,546 discloses partial and full prosthetic denture plates and processes to make them. A partial denture plate comprised of a denture base formed of a composite laminate having an intermediate layer of a woven fabric with non-woven veils disposed on opposite sides thereof is encapsulated in a polymeric resin. The denture base is moulded to conform to a shape of a patient's mouth. The denture base has at least one tab extending from the denture base. The tab is oriented to be in alignment with the patient's natural teeth. A synthetic tooth is moulded on each tab resulting in a denture device having a fiber-reinforced composite base and a synthetic tooth, or teeth, moulded on each tab, the tab or tabs made of and extending from the fiber-reinforced composite. Similarly, a full denture plate is disclosed. A rib is positioned on a parabolic strip of the composite laminate, the rib generally conforming to a patient's gum line. Artificial teeth are then moulded on the rib resulting in a full, prosthetic, denture plate.

U.S. Pat. No. 3,906,550 discloses a prosthetic devices for replacement, attachment and reconstruction of bone structure in skeletal systems of humans and animals. The prosthetic devices may be a fiber-metal structure of sufficient section to support loads adequately or may include a solid load-carrying member having a fiber-metal structure secured to the surface thereof. The fiber-metal structure is sintered and open-pored so that the bone and tissue into which the prosthetic device is implanted will grow into such fiber metal structure.

DE 41 33 690 discloses ready-made dental crowns and mastication surfaces, the occlusal halves of one or more crowns are moulded in the form of a plastic covering to existing metallic dental crowns, or to prosthetic constructions, and are applied to them by pressing with a finger or an instrument. The crowns have projections and depressions and are hardened after forming by polymerisation or sintering. The crown consists preferably of only a reinforcing layer between 0.5 and 5 mm thick in the shape of the mechanism surface. The plastic material may be pressure-, temperature- or light-hardening composites, or a plastic, or sintered metals or plastic-metal composites. In particular inorganic substances are used, and the material is reinforced with fibers or fabric preferably made of synthetic or natural fibers.

Some prior art documents thus disclose prepregs and composites wherein the reinforcing fibers project out from the surface. The drawbacks of the proposed prepregs and composites are however that either the fibers are at least partially covered by the matrix or the fibers have been revealed using mechanical treatment that partly destroys the fibers and in consequence decreases the mechanical strength of the fibers. The mechanical strength of a product manufactured by using such a prepreg is thus not accurate and specified.

OBJECT AND SUMMARY OF THE INVENTION

An object of the present invention is to provide prepreg and a composite that can be durably and firmly bonded to synthetic or living materials and used for medical and dental as well as technical applications, which prepreg and composite does not have the drawbacks listed above.

The present invention provides a prepreg according to the appended claims. The prepreg according to the invention comprises fibers and a curable matrix, and is characterised in that said prepreg has a core and a surface part encasing said core wherein the matrix of the core and of the surface part are made of a same material and in that the proportion of the matrix to the fibers is higher in the core than in the surface part.

The present invention further relates to a composite obtainable by curing the matrix of a prepreg according to the invention.

The present invention also relates to the use of a prepreg or composite according to the invention for medical and/or dental constructions, as well as in tools, devices and parts of instruments.

DETAILED DESCRIPTION OF THE INVENTION

By "curing" in this application it is meant both polymerising and crosslinking. Furthermore, by dendrimers large spherical hyper-branched polymers are meant. The word "impregnation" is also used in the meaning of "wetting" as will be apparent from the description below.

The present invention provides a prepreg comprising fibers and a curable matrix, and it is characterised in that said prepreg has a core and a surface part encasing said core wherein the matrix of the core and of the surface part are made of a same material and in that the proportion of the matrix to the fibers is higher in the core than in the surface part.

The prepreg according to the present invention thus concerns a prepreg having a core wherein the fibers are well impregnated with said curable matrix whereas the surface part has fibers partially or totally non-impregnated with said curable matrix.

The surface part wherein the proportion of the matrix is lower than in the core allows impregnation of the surface part with new material thus resulting in mechanical interlocking of the new material with the core of the prepreg. The newly impregnated interface layer acts as a stress-breaker layer by dividing the stress evenly within the layer thus diminishing the risk of debonding. It is to be noted that the interface between the core and the surface part of the prepreg may be distinct (sharp) or indistinct, according to whichever option is preferred for the final use of the prepreg.

The present invention thus provides a prepreg that bonds to other synthetic or living materials and forms a durable bond that is based on mechanical interlocking and adhesion of the prepreg to said synthetic or living material. The fibers on the surface of the prepreg are intact and not covered by the matrix and thus the strength of the resulting product can be determined in advance and the user can be certain that the strength of the product is as desired.

Furthermore, since the matrix of the inventive prepreg is in a curable form, the prepreg according to the present invention can be preformed for a specific use. In consequence, there are no limitations as to the size and shape of the prepreg and it may be used in any desired applications.

According to an embodiment of the invention, the proportion of the matrix to the fibers in the surface part is 0–95%, preferably 0–50%, more preferably 0–20% of the proportion of the matrix to the fibers in the core. In fact, the proportion of the matrix to the fibers in the surface part may be selected freely between 0 and 99% of the proportion of the matrix to the fibers in the core. It may for example be 2%, 6%, 13%, 23%, 36%, 41%, 57%, 63%, 70%, 82% or 92%.

According to another embodiment of the present invention, the density of the matrix is higher in the core than in the surface part, that is, the matrix of the surface part is porous or its porosity is higher than the porosity of the core. In other words, an essential portion of the volume of the matrix of the surface part is occupied by voids and/or pores.

As was discussed above, the interface between the core and the surface part may be either distinct or indistinct. In the case the interface is distinct, the thickness of the surface part may be freely selected. According to an embodiment of the invention, said thickness is 1–50%, preferably 1–30% of the total thickness of the prepreg. Said thickness can obviously be freely selected. In any case, the thickness of the surface part is selected such that the desired mechanical strength is obtained in the final product.

According to an embodiment of the present invention, the fibers of the core are essentially unidirectional and continuous, the fibers of the surface part may be in the form of a tubular braid encasing the core. According to a preferred embodiment of the invention, the fibers of the surface part are essentially perpendicular to the essentially unidirectional and continuous fibers of the core. The fibers of the surface part can also form a brush-like surface and/or a surface with fiber loops as will be shown in the Figures.

According to a further embodiment of the present invention, the matrix of the surface part and/or the fibers of the surface part can be functionalised. If the fibers are functionalised, said functionalisation is typically made to the surface of the fibers. The fibers can be functionalised with e.g. silane, titanate, zirconate or aluminate. The matrix of the surface part can be functionalised with e.g. hydroxyapatite, silica or titanium.

The functionalisation of the fibers further increases the bonding of the prepreg to the surrounding material and emphasises the need for the fibers to be uncovered and undamaged.

According to the present invention, the fibers may be selected from a group consisting of inert glass fibers, bioactive glass fibers, carbon/graphite fibers, aramid fibers, poly(p-phenylene-2,6-benzobisoxazole) fibers (PBO), poly (2,6-diimidazo(4,5-b4',5'-e)pyridinylene-1,4(2,5-dihydro) phenylene fibers (PIPD), polyolefin fibers such as polyethene or polypropene fibers, sol-gel processed silica fibers collagen, cellulose and modified cellulose fibers. Any combination of said fibers may be used. Poly(p-phenylene-2,6-benzobisoxazole) fibers and poly(2,6-diimidazo(4,5-b4',5'-e)pyridinylene-1,4(2,5-dihydro)phenylene fibers belong to a group called rigid-rod polymer fibers. It is obvious to a person skilled in the art that any other known fibers may be used in the present invention, provided it is possible to obtain a suitable adhesion between said fibers and matrix, in order to achieve the desired mechanical properties.

The matrix of the prepreg may comprise monomers selected from the group consisting of methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate TEGDMA), diurethane dimethacrylate, 2,2-bis(4-(2-hydroxy-3-methacryloxy)phenyl)propane (BisGMA), methacrylate functionalized dendrimers, other methacrylated hyperbranched oligomers and mixtures thereof. The matrix may also be made of crosslinkable monomers or polymers such as E-caprolactone, polycaprolactone, polylactides, polyhydroxyproline, and other biopolymers as well as polyamides, polyurethane, polyethylene, polypropylene, other polyolefins and polyvinyl chloride (PVC). The matrix may naturally also consist of a mixture of a monomer(s) and a polymer(s). According to an embodiment of the invention, said curable monomer system is a monomer or a mixture of monomers having low viscosity.

According to yet another embodiment of the invention, the surface part of the prepreg may additionally comprise a bioactive agent, a filler or the prepreg according to the present invention may comprise a surface part comprising biomimetically apatite coated fibers improving bone growth into the spaces between the fibers. The surface part or the apatite coated fibers of the surface part can comprise or can be impregnated with a particulate filler of e.g. bioactive glass, other additives, such as silicon (Si), calcium (Ca), phosphorus (P), barium (Ba), magnesium (Mg), potassium (K), sodium (Na), titanium (Ti) or fluorine (F) oxides or other compounds of said elements, colour pigments, inert ceramics, hydroxyapatite or other calcium phosphates, xerogels, functionally bioactive or therapeutically active substances, growth factors, antigens, antibiotics, disinfectants, radio opaque materials, bone morphogenic proteins (BMPs), interferons, corticosteroids, biphosphonates, cytostatics, anabolic hormones, vitamins, anti-inflammatory agents, antimicrobiotics and combinations and mixtures thereof. This is to be taken as a non-limiting list of examples and a person skilled in the art is able to find more examples of suitable active agents.

The prepreg according to the present invention may be manufactured in different ways. One way is a process comprising the steps of
 a) impregnating fibers with a curable matrix,
 b) dissolving a part of said matrix with a solvent and
 c) removing said solvent.

The removal of the solvent in step c) is made for example by washing. It is also possible to make the above step b) by dipping the impregnated fibers into the solvent and thus the solvent is removed simply by removing the prepreg from the solvent. The viscosity of the matrix is chosen such that this process is possible to use, i.e. the viscosity of the matrix is high enough to enable this dipping procedure. An alternative way of manufacturing the inventive prepreg is to use as matrix a combination of different materials, one of which evaporates in ambient temperatures. A prepreg according to the present invention is thus obtained by allowing said material to evaporate from the surface of the prepreg. An example of such a combination of matrix materials is methyl methacrylate and BisGMA, wherein methyl methacrylate evaporates from the surface of the prepreg. The combination preferably also includes a curing agent, for example a curing agent that is activated by light.

The invention further relates to a composite obtainable by curing the matrix of a prepreg according to the invention. The invention also relates to a composite obtainable by further impregnating the prepreg according to the invention with another curable matrix, possible comprising fibers and/or fillers and by curing the obtained impregnated prepreg.

The prepreg and composite according to the present invention may be in any desired form such as sheets, strips, cubes, spheres, discs etc.

The composite or prepreg according to the invention can be used for medical and/or dental constructions. In dentistry the prepregs and composites according to the present invention may be used for example in endosseous prostheses, maxillofacial prostheses, dental implants, dental bridges, resin-bonded bridges, framework materials for fixed partial dentures, dentures, periodontal splints, root canal posts, orthodontic appliances, crowns, fillings, mouth guards, matrices and inserts for dental filling material, reinforcements for removable dentures, repair materials for gold alloy bridges, materials for bite registration index, external orthopedic supporting devices and sport devices. In the field of medicine and surgery, the present prepregs and composites can be used in bandages replacing traditional gypsum plasters, in endosseus implants as a framework material for prostheses, bone support plaster replacements and a surface material for improved bone retention.

The present composites and prepregs can also be used in tools, devices and parts of instruments as well as components for adhesives. An example of non-medical use of the present prepreg could be for example as wallpaper or other surface covering purposes, wherein a sheet of a prepreg or composite according to the present invention may be attached to a wall and a layer of plaster added on top of said sheet, thus making it easy to form surfaces having any desired patterning in three dimensions.

DETAILED DESCRIPTION OF THE DRAWINGS

Figure 1:
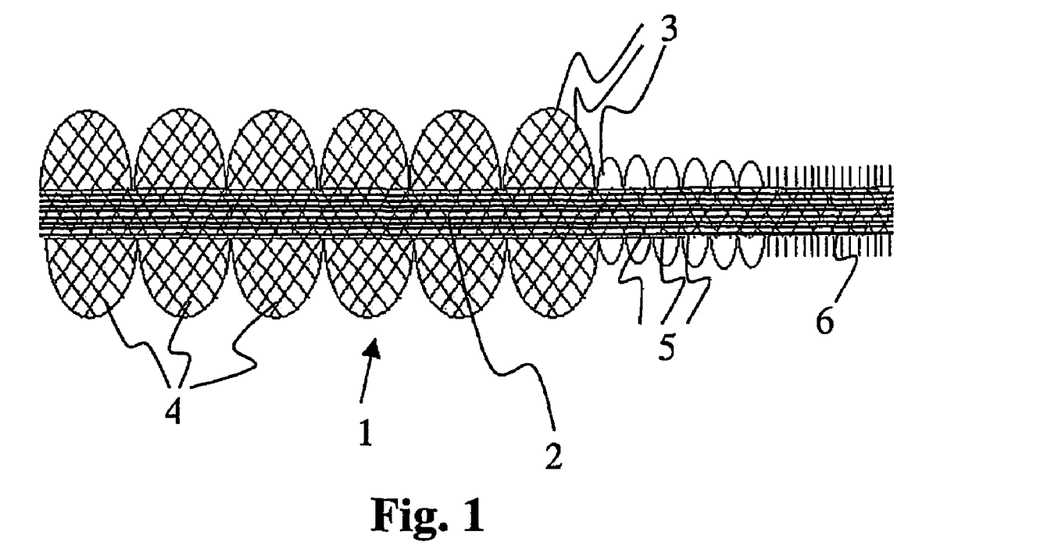
FIG. 1 schematically illustrates a prepreg according to a first embodiment of the invention.

FIG. 1 schematically illustrates a prepreg according to a first embodiment of the invention, where the prepreg 1 comprises essentially continuous fibers 2 of the core and fibers 3 of the surface part, wherein the fibers 2 of the core have been impregnated with a matrix and the fibers 3 of the surface part have been only partially impregnated with a matrix. In this embodiment, the fibers 3 of the surface part are in the form of a tubular braid and said braid is arranged so as to form sequential bulges 4 as well as fiber loops 5 and a brush-like surface 6. The fibers of the surface part have been revealed by dissolving the matrix of the surface part with a suitable solvent.

Figure 2A:
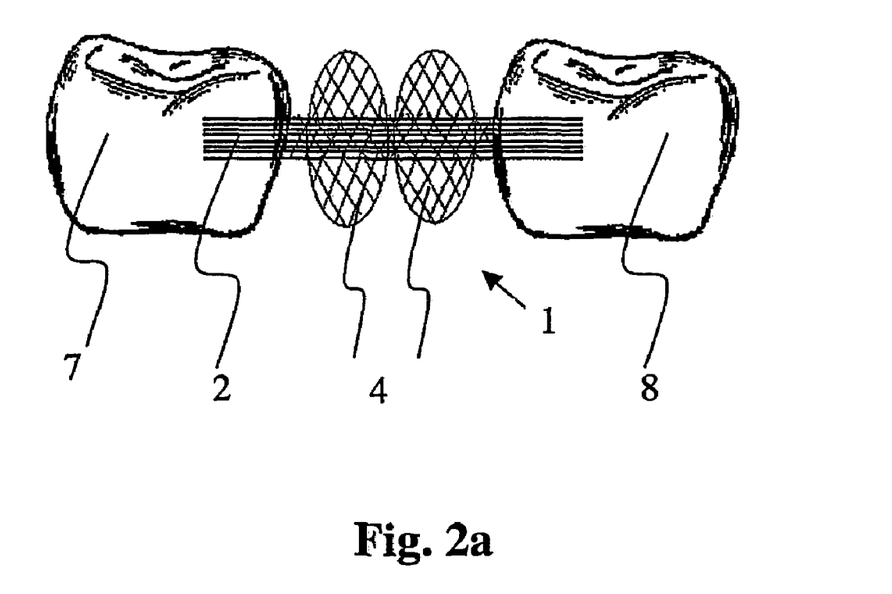
FIGS. 2a and 2b illustrate the use of a prepreg according to a second embodiment the invention.
Figure 2B:
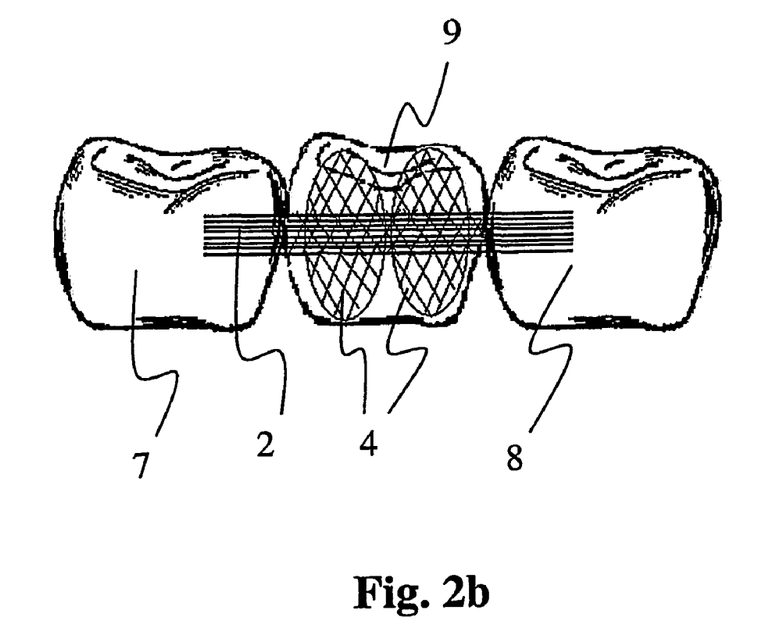

FIGS. 2a and 2b illustrate the use of a prepreg according to a second embodiment the invention. In this embodiment, the prepreg is used for the construction of a fixed partial denture. In a first step, a prepreg 1 is formed on a plaster mould and fibers are revealed as explained above. This prepreg 1 is then fixed on supporting teeth 7 and 8 as illustrated in FIG. 2a and the prepreg is reimpregnated with a dental monomer and polymerised. In a further step, the shape and colour of a tooth is achieved using veneering composite 9 as shown in FIG. 2b.

Figure 3:
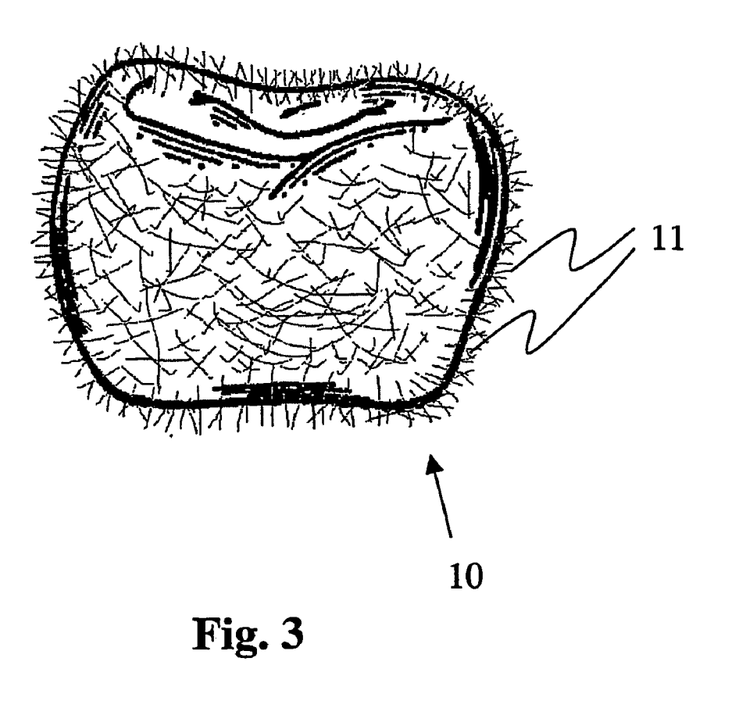
FIG. 3 illustrates the use of a prepreg according to a third embodiment of the invention.

FIG. 3 illustrates the use of a prepreg according to a third embodiment of the invention as a preformed tooth 10 which manufacturing process is described below in Example 4. The Figure shows the fibers 11 of the surface that project out of the solid surface of the preformed tooth.

Figure 4:
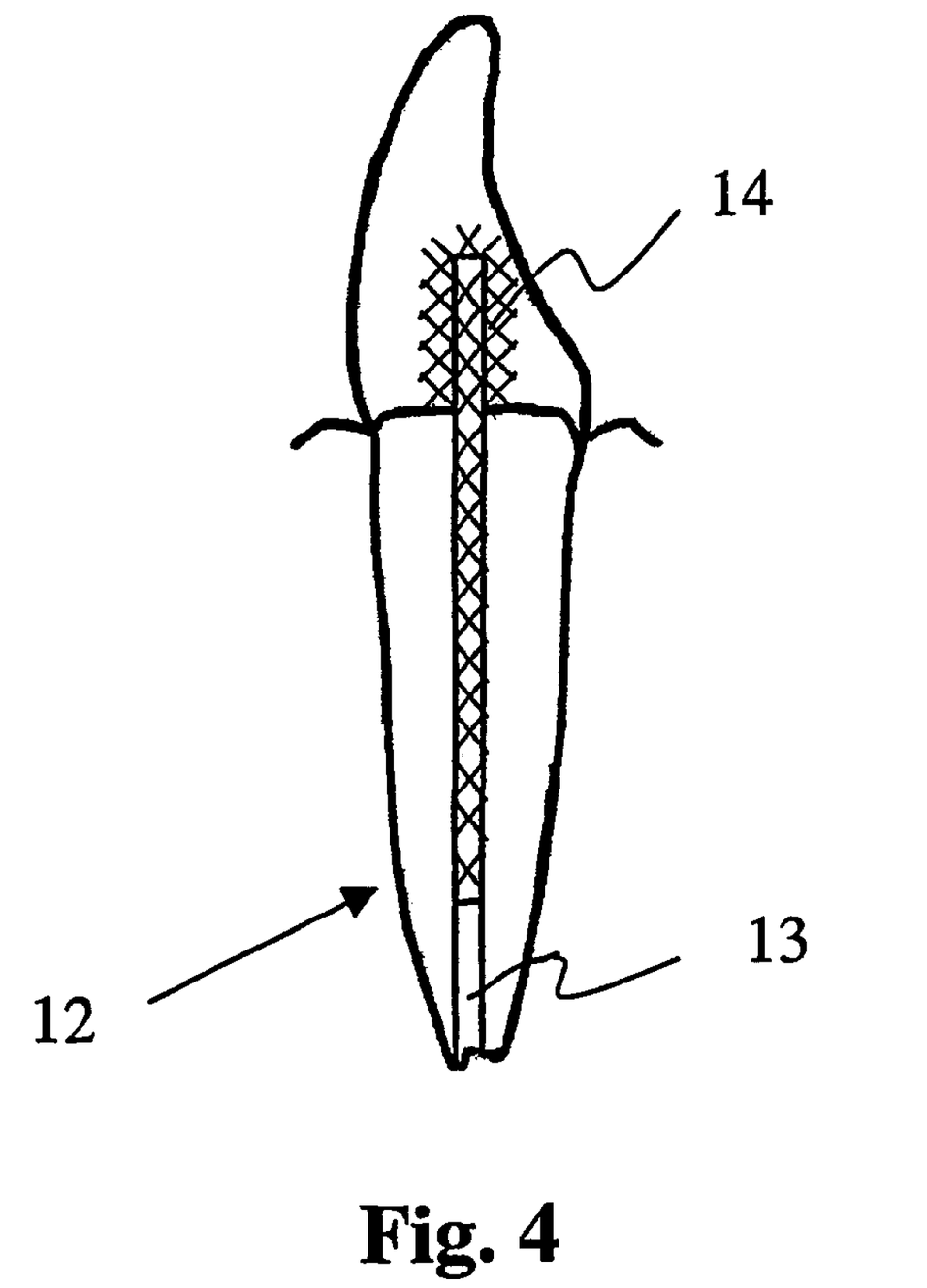
FIG. 4 illustrates the use of a prepreg according to a fourth embodiment of the invention.

FIG. 4 illustrates the use of a prepreg according to a fourth embodiment of the invention for the manufacturing of a root canal post 12. In this embodiment, a bundle of long continuous fibers 13 are surrounded with a braid 14, which is impregnated with a thick matrix comprising photo-initiators. The surface of the braid 14 is treated with a solvent so that a porous fiber structure is revealed. The porous fiber structure increases bonding which is essential in the crown end of the post. Bioactive or therapeutically active elements such as bioactive glass fillers can also be included in the porous surface of the root channel. Before cementing the post into the root channel, the post is reimpregnated with dental cement.

Figure 5:
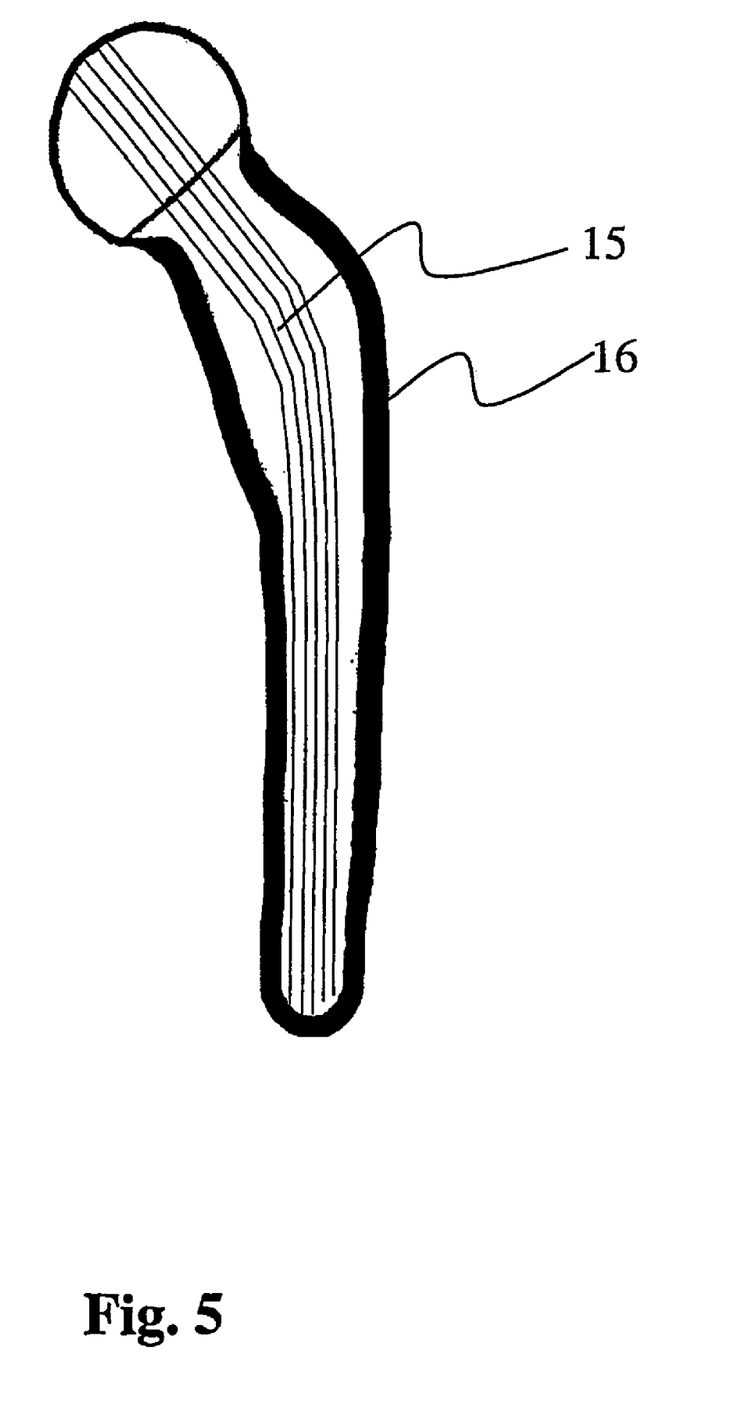
FIG. 5 illustrates the use of a prepreg according to a fifth embodiment of the invention.

FIG. 5 illustrates the use of a prepreg according to a fifth embodiment of the invention as a hip prosthesis. In this embodiment, the prepreg comprises a core 15 comprising of a long continuous E-glass fiber rowing. This core 15 is surrounded with a three-dimensional fabric made of suitable fibers and the core and the fabric are tied together with fiber yarn. The obtained preformed hip prosthesis is impregnated with a thick matrix, and the fiber surface is revealed as explained above, by using a suitable solvent. The prepreg is then polymerised in the desired shape to form a composite. The fibers of the surface part 16 are then coated with hydroxyapatite and the surface part may then be further impregnated with a particulate filler consisting of bioactive glass.

Figure 6A:
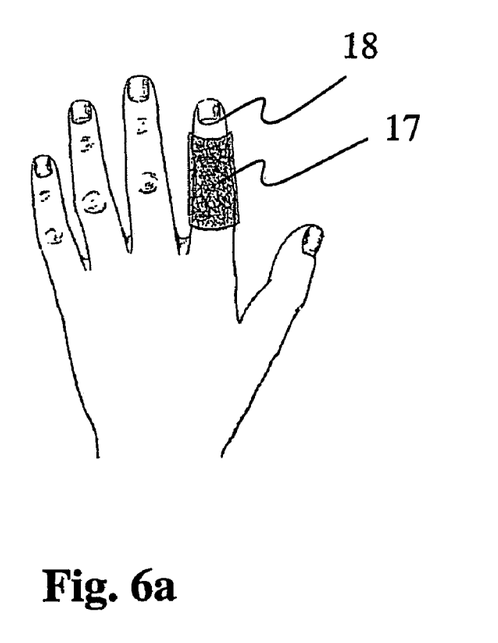
FIGS. 6a and 6b illustrate the use of a prepreg according to a sixth embodiment of the invention.
Figure 6B:
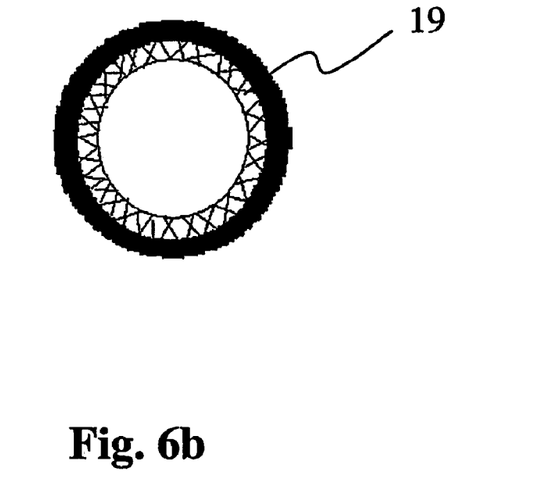

FIGS. 6a and 6b illustrate the use of a prepreg according to a sixth embodiment of the invention as replacement of plaster for bone support. In this embodiment, a round hollow shape, i.e. a tube, was formed using long continuous fibers on the outer surface of the tube and a braid on the inner surface of the tube. The fibers on the outer surface were revealed as above. The prepreg 17 obtained can then be used on e.g. a finger 18 and polymerised with light to give support during e.g. bone healing. Whereas the prepreg 17 has a porous inner surface 19, air can flow through the support. This approach can be used for supporting many parts of the body, such as knees, femur, ulnar and radius etc., during bone healing.

Figure 7:
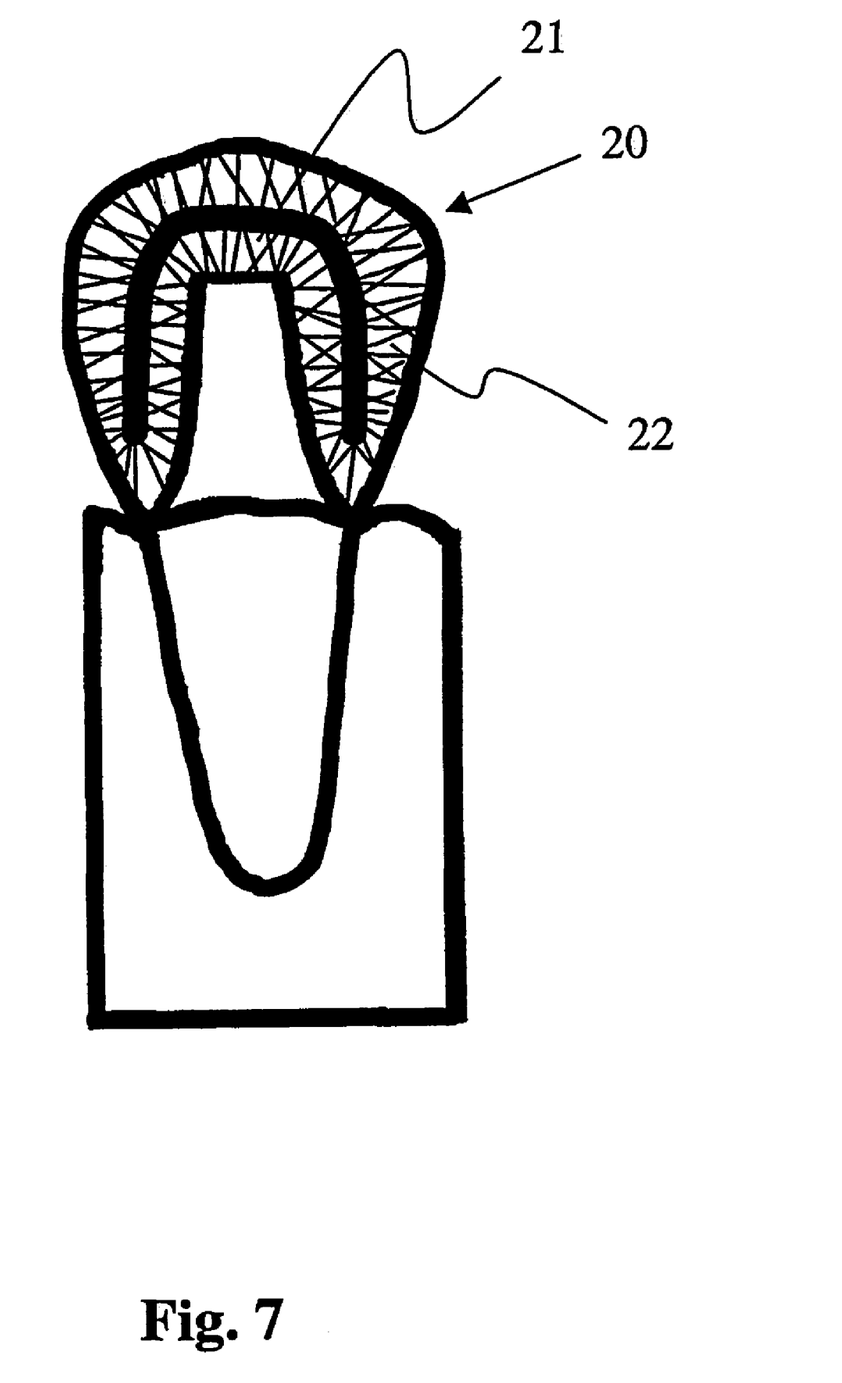
FIG. 7 illustrates the use of a prepreg according to a seventh embodiment of the invention.

FIG. 7 illustrates the use of a prepreg according to a seventh embodiment of the invention as dental crown. In this embodiment, a three-dimensional fiber fabric is preformed into the shape of a premolar crown 20 as in FIG. 3 above, impregnated with a thick matrix and fibers on both the inner and outer surfaces of the fabric are revealed using a solvent. The abundantly impregnated inner structure 21 is then polymerised, so that a stiff, moderately pressure resistant structure is formed. The revealed fibers of the outer surface 22 are then impregnated with a dental filler composite, e.g. a restorative or veneering composite. A dental polymer cement is then applied to the inner side of the crown structure and pushed on the pontic. After the right shape is achieved, the side of the crown is polymerised with light. Occlusal contact is taken by letting the patient close his/her mouth and the polymerisation of the crown structure is initiated by light, leading to a finished crown.

Figure 8A:
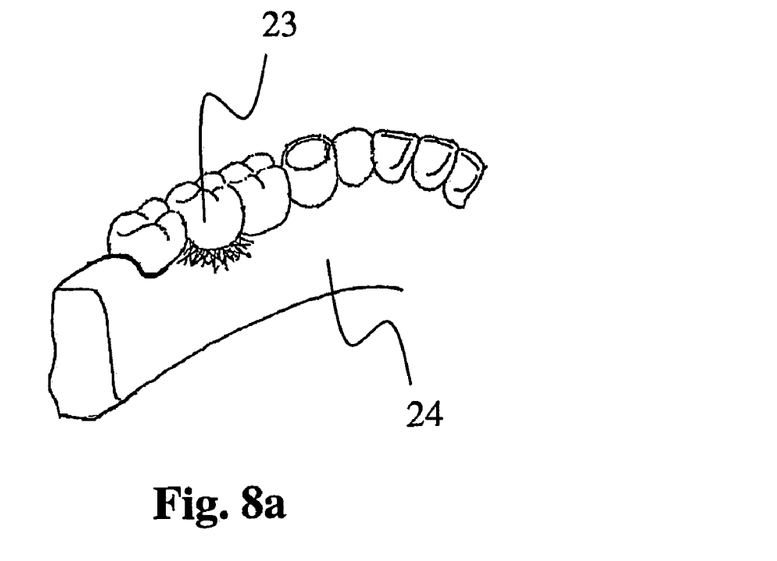
FIGS. 8a and 8b illustrate the use of a prepreg according to an eighth embodiment of the invention.

FIGS. 8a and 8b illustrate the use of a prepreg according to an eighth embodiment of the invention as a tooth for an artificial denture. In this embodiment, a prepreg tooth as in FIG. 3 is used as a repair of a denture after an original tooth of the denture has been detached. The revealed fiber structure of a prepreg tooth is impregnated with a suitable second matrix so that the fibers of the outer part are used to increase bonding between the tooth 23 and the denture plate 24 as shown in FIG. 8a. At the same time, the fibers of the outer part of the prepreg increase the toughness of the denture plate at the place of repair and thus eliminate fatigue fractures at that place.

Figure 8B:
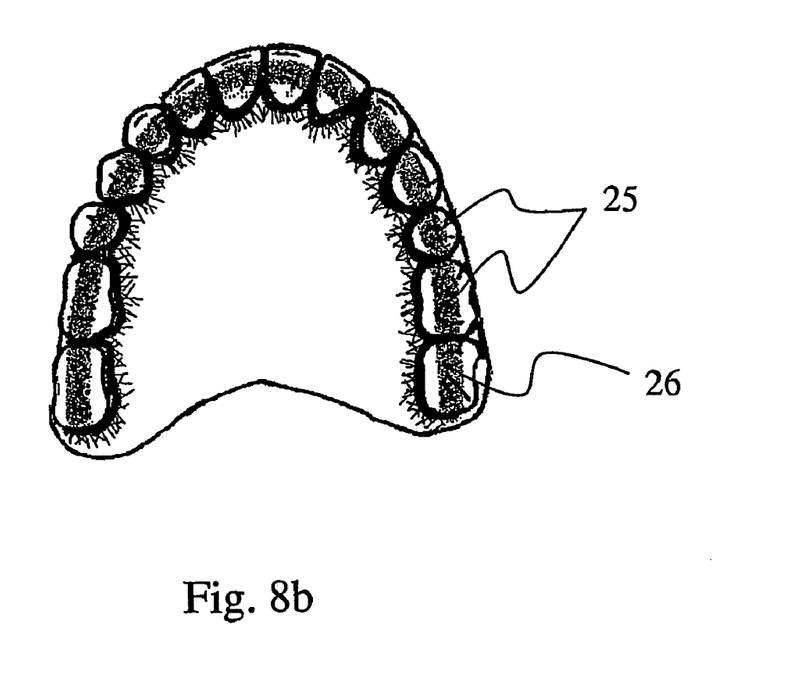

If all the teeth of a denture are replaced with fiber prepreg teeth according to the present invention, the entire denture is advantageously reinforced with fibers. The prepreg teeth 25 according to this invention can also be tied together with long continuous fibers 26 as shown in FIG. 8b and a dentist or dental technician can use this tooth set as part of a setting in the laboratory or in the mouth of the patient.

Figure 9:
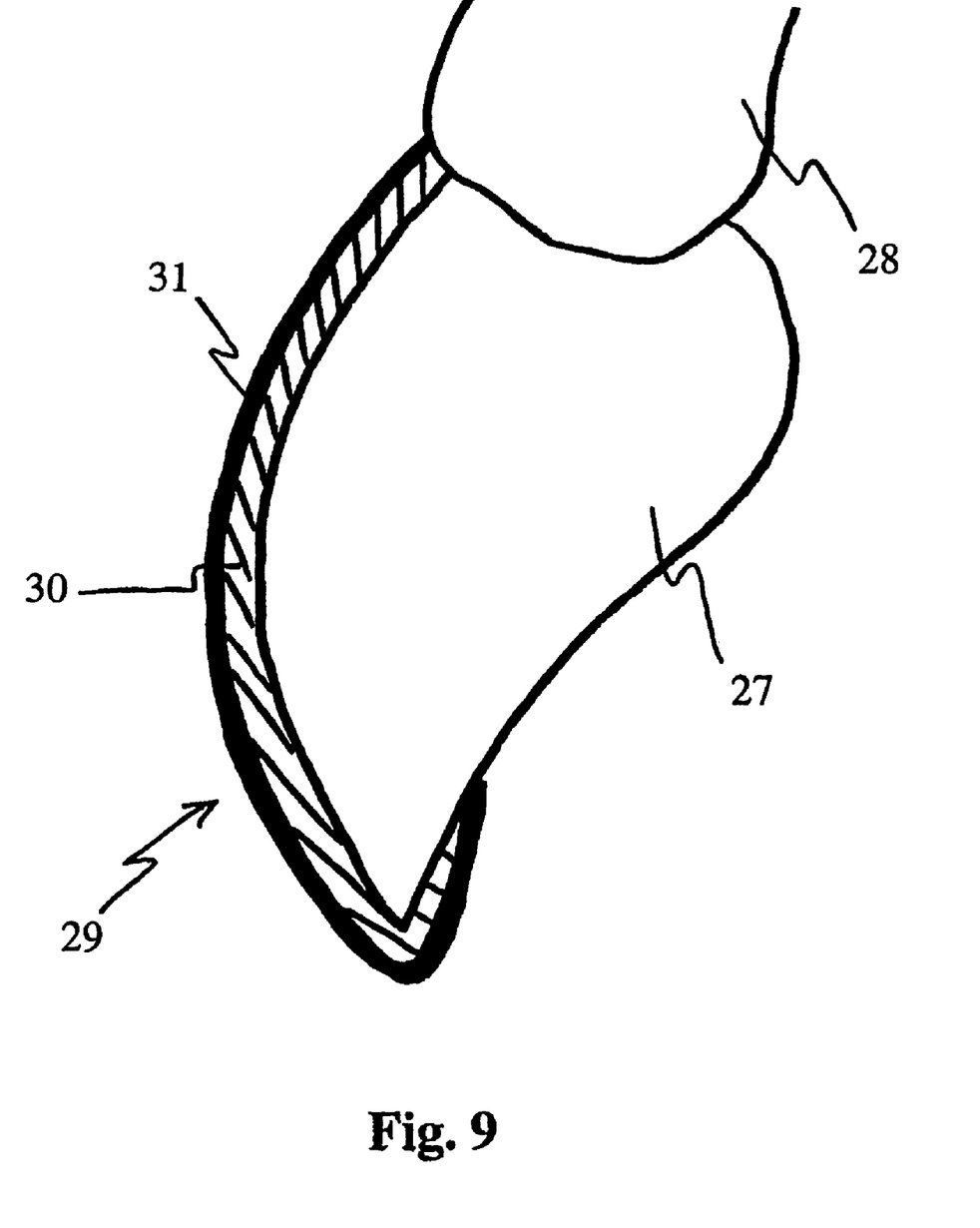
FIG. 9 illustrates the use of a prepreg according to a ninth embodiment of the invention.

FIG. 9 illustrates the use of a prepreg according to a ninth embodiment of the invention as a coating for a tooth. The Figure shows a tooth 27 and gingiva 28. The tooth 27 has been covered by a prepreg 29 according to the invention in such a way that a sheet of a prepreg having a revealed fiber structure on both sides of said sheet is positioned on the surface to be covered. The first surface 30 of the prepreg is not impregnated with another matrix but is positioned on the surface of the tooth, which surface has been treated in an appropriate manner to provide for a strong bond to said prepreg. This treatment may be for example application of a dental cement. The second surface 31 of the prepreg has been or is impregnated with a product that provides a final surface that has an appropriate colour and sufficient mechanical properties. This second surface 31 may be prepared outside the patient's mouth thus leading to a covering element having approximately the shape of the tooth to be covered. During the positioning of such a covering element on the tooth, the first surface of the prepreg is deformable enough to allow an exact positioning of the covering element.

Figure 10:
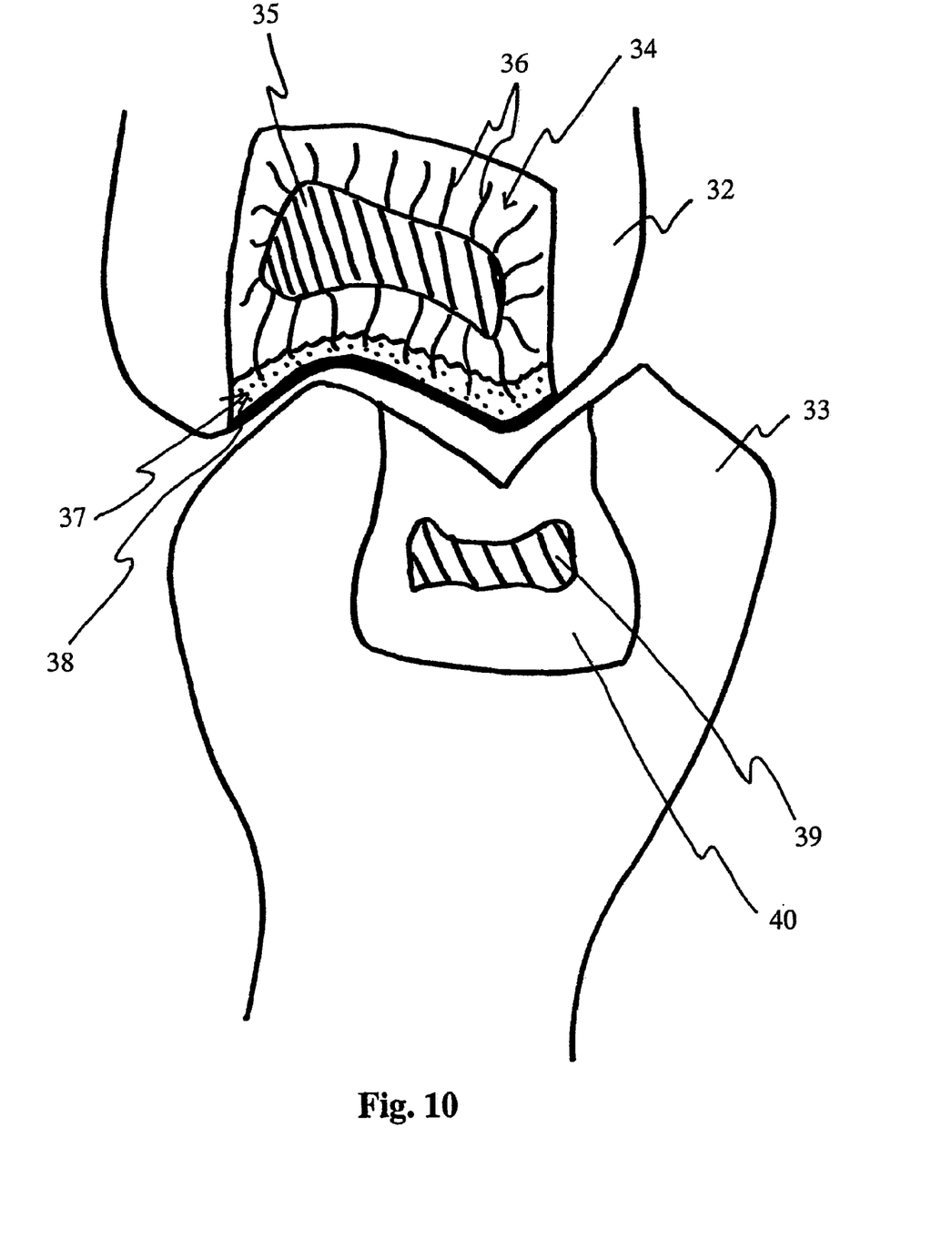
FIG. 10 illustrates the use of a prepreg according to a tenth embodiment of the invention.

FIG. 10 illustrates the use of a prepreg according to a tenth embodiment of the invention. This Figure shows two teeth 32 and 33 both having cavities that have been filled with a prepreg according to the present invention. The cavity of the tooth 32 has been firstly partially filled with a first prepreg 34 having a dense core 35 and a porous outer surface part where the fibers 36 (shown schematically) project out from the surface of the core. This first prepreg has then been covered by a second prepreg 37 wherein the outer surface of the first prepreg is partially impregnated with said second prepeg 37. The surface of the second prepreg 37 that forms the outer surface of the tooth is covered by a third component that provides for a hard and stiff surface 38.

The cavity of the second tooth 33 has been filled with a prepreg according to the present invention, having a core 39 and a surface part 40.

The invention is illustrated by the following examples. In the examples the invention is explained in terms of preferred embodiments and implications in dentistry even though the invention can also have other medical and technical implications.

EXPERIMENTAL PART

EXAMPLE 1

A prepreg is manufactured using a thick matrix system of BisGMA 70 wt-%, poly(methyl methacrylate) (PMMA) 15 wt-%, MMA 14 wt-%, a photoinitiator system camphorquinone (CQ, by Fluka) 0.5 wt-% +2-(dimethyleneamino)ethyl methacrylate (DMAEMA by Aldrich) 0.5 wt-%. The prepreg comprises long continuous E-glass fibers in the core and the long continuous fibers are surrounded with a tubular fiber E-glass braid (Eurocarbon, Holland). The system is then impregnated with the above thick matrix system. Impregnated fibers on the outer surface are revealed by dissolving the matrix of the surface part with tetrahydrofuran (THF).

EXAMPLE 2

A prepreg is manufactured using the thick matrix system of Example 1. The prepreg comprises long continuous E-glass fibers in the core and these long continuous fibers are surrounded with a thin three-dimensional E-glass fabric (Parabeam, Holland). The core and the fabric sheath are tied together with E-glass yarn and system obtained is impregnated with the matrix. Impregnated fibers on the outer surface are revealed by dissolving the matrix of the surface part with THF.

EXAMPLE 3

A thick matrix system is used as in examples 1 and 2 above to impregnate E-glass wool (30 vol-% of E-glass with respect to the total volume) having the shape of a tooth. Impregnated fibers on the outer surface are revealed by dissolving the matrix of the surface part with THF. The inner structure with fibers is polymerised to obtain a stiff core. The fibers or the surface which are not covered by polymerised matrix are then reimpregnated with another matrix system.

EXAMPLE 4

A preformed fiber reinforced tooth is manufactured using E-glass fiber wool coated with heat curable thermoset acrylate. The E-glass fiber wool is inserted in a tooth mould and heated at 200° C. for 15 min. The preformed fiber-tooth obtained has a highly porous fiber structure and it can be impregnated easily with a thick resinous light curable resin (as in example 1) using warming and underpressure. After the preformed tooth is impregnated, it is shortly dipped into THF. This is done in order to dissolve a thin layer of the thick resin from the surface so that fibers are exposed at the surface and these fibers are used as a mechanical interlocking component to increase the bonding between the pre-impregnated, preformed fiber reinforced tooth and a veneering composite. Before polymerisation the tooth is easily shapable and can be used as a "ready for use"-part for a tooth bridge. The polymerisation of the preformed fiber reinforced tooth tooth may be initiated with light for example. The veneering composite is added and then polymerised. These steps of adding the veneering composite and polymerisation may be done either on a model or in the patient's mouth.

EXAMPLE 5

A round hollow shape, i.e. a tube, was formed using long continuous fibers and having a braid inside. The tube obtained was impregnate with a thick matrix and the product was dipped into a solvent in order to reveal the fiber structure on the outer part. The prepreg was further coated with a PMMA film by dipping it fast into THF solution of PMMA (THF 90 wt-% +PMMA 10 wt-%).

EXAMPLE 6

A prepreg tooth as in example 4 was used as a repair of a denture after an original tooth of the denture was detached. The revealed fiber structure of the prepreg tooth was impregnated with PMMA as described in U.S. Pat. No. 5,846,640.

EXAMPLE 7

Silanised E-glass fiber wool (30 vol-% of E-glass with respect to the total volume) was impregnated with a thick matrix producing a paste, which can be considered a restorative mount paste. A thin layer of non-impregnated fiber wool surface was revealed by dissolving the matrix. The dentin surface was etched with 35% phosphoric acid for 15 seconds and dentin primer was applied to the dentin. The restorative paste was impregnated with a dental adhesive and the paste was pressed against the tooth to be restored and photopolymerised. The surface of the restorative basement filling thus obtained was covered with a suitable product to form the surface of the tooth.

EXAMPLE 8

Shear bond strength test according to ISO/TR 11405 was used to measure bonding properties of a prepreg according to the present invention. Prepregs according to the invention were compared to a control group consising of fully impregnated unidirectional E-glass fibers. The samples were photopolymerized with a light-curing unit (Optilux 501) for 40 seconds. Stub (diameter 3.6 mm) of filler particle composite (Gradia, CG Corporation, Tokyo, Japan) was used as an adherend and was photopolymerized (Optilux 501) for 40 seconds on the samples.

Shear bond strength was measured using a crosshead speed of 1.0 mm/min. Half of the samples were stored in dry condition and half of the samples were exposed to thermal cycling (5–55° C., 6000 cycles, bath time 20 seconds) in distilled water in order to produce an accelerated ageing test.

Figure 11:
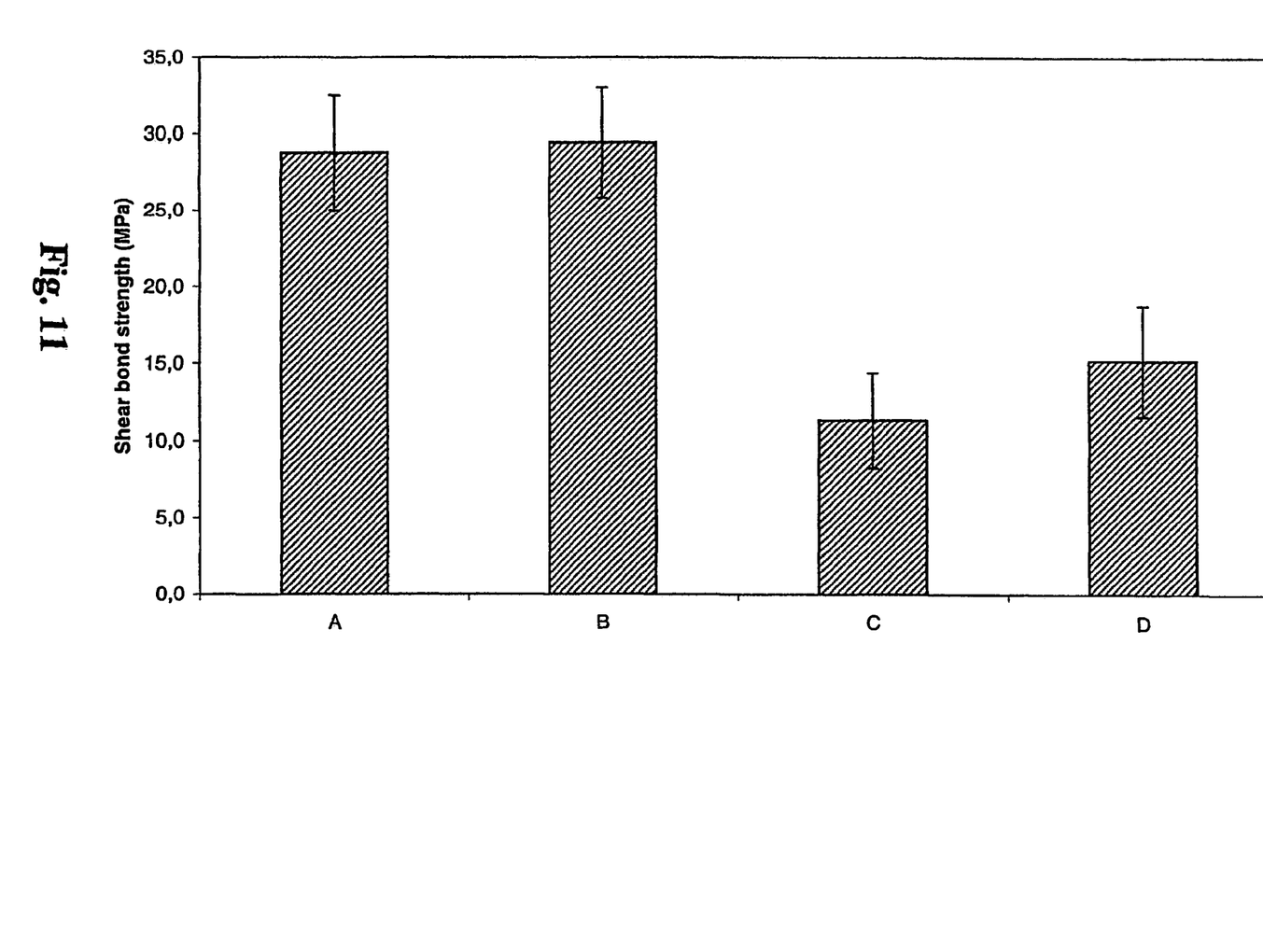
FIG. 11 illustrates the results obtained in Example 8.

The results of the tests are shown in FIG. 11, where the sample A is a dry prepreg according to the invention, B is a thermocycled prepreg according to the invention, C is a dry unidirectional conventional prepreg and D is a thermocycled unidirectional conventional prepreg. It can be clearly seen that the shear bond strength of the prepregs according to the present invention is considerably higher than the shear bond strength of the conventional prepreg.

In this specification, except where the context requires otherwise, the words "comprise", "comprises" and "comprising" means "include", "includes" and "including", respectively. That is, when the invention is described or defined as comprising specified features, various embodiments of the same invention may also include additional features.

It will be apparent to those skilled in the art that various other applications and modifications of the method of the present invention of utilizing a fiber structure to increase bonding between stiff and flexible materials and prepregs to form reinforced structures for various dental and medical applications can be provided by the invention.

In view of the above, the present invention may be embodied in other specific forms without departing from the spirit or essential attributes thereof and, accordingly, reference should be made to the appended claims, rather than to the foregoing specification as indicating the scope of the invention.

The invention claimed is:

1. A prepreg comprising fibers and a curable monomer, crosslinkable monomer or polymer, wherein said prepreg has a core and a surface part encasing said core, wherein the monomer, crosslinkable monomer or polymer of the core and of the surface part are made of a same material, and wherein the proportion of the monomer, crosslinkable monomer or polymer to the fibers is higher in the core than in the surface part.

2. The prepreg of claim 1, wherein the proportion of the monomer, crosslinkable monomer or polymer to the fibers in the surface part is 0–95% of the proportion of the monomer, crosslinkable monomer or polymer to the fibers in the core.

3. The prepreg of claim 1, wherein the proportion of the monomer, crosslinkable monomer or polymer to the fibers in the surface part is 0–50% of the proportion of the monomer, crosslinkable monomer or polymer to the fibers in the core.

4. The prepreg of claim 1, wherein the proportion of the monomer, crosslinkable monomer or polymer to the fibers in the surface part is 0–20% of the proportion of the monomer, crosslinkable monomer or polymer to the fibers in the core.

5. The prepreg of claim 1, wherein the density of the monomer, crosslinkable monomer or polymer is higher in the core than in the surface part.

6. The prepreg of claim 1, wherein the thickness of the surface part is 1–50% of the total thickness of the prepreg.

7. The prepreg of claim 1, wherein the thickness of the surface part is 1–30% of the total thickness of the prepreg.

8. The prepreg of claim 1, wherein fibers of the core are essentially unidirectional and continuous.

9. The prepreg of claim 1, wherein the fibers of the surface part are in the form of a tubular braid encasing said core.

10. The prepreg of claim 8, wherein fibers of the surface part are essentially perpendicular to said essentially unidirectional and continuous fibers of the core.

11. The prepreg of claim 1, wherein the fibers of the surface part form a brush-like surface and/or a surface with fiber loops.

12. The prepreg of claim 1, wherein the material of said monomer, crosslinkable monomer or polymer is selected from the group consisting of methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate, 2,2-bis(4-(2-hydroxy-3-methacryloxy)phenyl)propane, methacrylate functionalized dendrimers, other methacrylated hyperbranched oligomers ε-caprolactone, polycaprolactone, polylactides, polyhydroxyproline, polyamides, polyurethane, polyolefins, polyvinyl chloride, mixtures and blends thereof.

13. The prepreg of claim 1, wherein said fibers are selected from a group consisting of inert glass fibers, bioactive glass fibers, carbon/graphite fibers, aramid fibers, poly(p-phenylene-2,6-benzobisoxazole) fibers, poly(2,6-diimidazo(4,5-b4', 5'-e)pyridinylene-1,4(2,5-dihydro)phenylene fibers, polyolefin fibers, collagen, cellulose and modified cellulose fibers.

14. The prepreg of claim 1, wherein the surface of the fibers of the surface part is functionalised.

15. The prepreg of claim 14, wherein the surface of the fibers of the surface part is functionalised with silane, titanate, zirconate and/or aluminate.

16. The prepreg of claim 1, wherein the monomer, crosslinkable monomer or polymer of the surface part is functionalised.

17. The prepreg of claim 16, wherein the monomer, crosslinkable monomer or polymer of the surface part is functionalised with hydxoxyapatite, silica and/or titanium.

18. The prepreg of claim 1, wherein the surface part further comprises a bioactive agent.

19. The prepreg of claim 18, wherein said bioactive agent is selected from a group consisting of bioactive glass, growth factors, bisphosphonates, antimicrobial agents, anti-inflammatory agents, bone morphogenic proteins, interferons, corticosteroids, cytostatics, anabolic hormones, vitamins, disinfectants and mixtures thereof.

20. A composite prepared by curing the monomer, crosslinkable monomer or polymer of a prepreg according to claim 1.

21. A method for preparing a medical and/or dental construction, comprising incorporating the prepreg of claim 1 into said construction.

22. A method for preparing a medical or dental construction, comprising incorporating the composite of claim 20 into at least one construction selected from the group consisting of endosseous prostheses, maxillofacial prostheses, dental implants, dental bridges, resin-bonded bridges, dentures, periodontal splints, root canal posts, orthodontic appliances, crowns, fillings, mouth guards, matrices and inserts for dental filling material, reinforcements for removable dentures, repair materials for gold alloy bridges, materials for bite registration index, bone support plaster replacements, external orthopedic supporting devices and sport devices.

* * * * *